United States Patent [19]

Wu

[11] Patent Number: 5,162,597
[45] Date of Patent: Nov. 10, 1992

[54] OLEFIN DISPROPORTIONATION AND APPLICATION THEREOF

[75] Inventor: An-hsiang Wu, Bartlesville, Okla.

[73] Assignee: Phillips Petroleum Company, Bartlesville, Okla.

[21] Appl. No.: 794,102

[22] Filed: Nov. 18, 1991

[51] Int. Cl.$^5$ .............................. C07C 6/04; C07C 7/00
[52] U.S. Cl. .................................... 585/646; 585/855; 585/867; 585/868
[58] Field of Search ............... 585/643, 646, 809, 853, 585/855, 868, 867

[56] References Cited

U.S. PATENT DOCUMENTS

| | | | |
|---|---|---|---|
| 3,637,891 | 1/1972 | McGrath et al. | 585/646 |
| 3,673,114 | 6/1972 | Allum et al. | 585/646 |
| 3,689,589 | 9/1972 | Reusser | 585/646 |
| 3,965,206 | 6/1976 | Montgomery et al. | 585/804 |
| 4,046,832 | 9/1977 | Nowak et al. | 585/646 |
| 4,217,299 | 8/1980 | Nakamura et al. | 260/464 |
| 4,754,098 | 6/1988 | Drake | 585/643 |
| 4,996,386 | 2/1991 | Hamilton et al. | 585/670 |

OTHER PUBLICATIONS

Kirk-Othmer Encycl. Chem. Technol. vol. 23, pp. 430–432, 1979, discloses the preparation of alkali metal and ammonium metatungstates and the use of paratungstate as catalyst.

Kirk-Othmer Encycl. Chem. Technol. vol. 8, pp. 597–598, 1979, discloses using carbene-bearing complexes such as diphenylcarbenetungsten pentacarbonyl as catalyst for olefin metathesis.

Primary Examiner—Anthony McFarlane
Attorney, Agent, or Firm—Lucas K. Shay

[57] ABSTRACT

A disproportionation catalyst comprising an ammonium or an alkali metal tungsten oxide and a process for forming disproportionation product using the disproportionation catalyst are disclosed. The disproportionation process is used to facilitate the separation of at least one 1-olefin from a mixture of olefins that have close boiling points by contacting the mixture of olefins with another 1-olefin under disproportionation conditions to produce disproportionation products which have significantly different boiling points among themselves and can be easily separated by conventional means.

27 Claims, No Drawings

OLEFIN DISPROPORTIONATION AND APPLICATION THEREOF

FIELD OF THE INVENTION

The invention relates to the disproportionation of olefins. It also relates to the separation of olefins that are difficult to separate by conventional means.

BACKGROUND OF THE INVENTION

The disproportionation or metathesis of olefins is a reaction in which one or more olefinic compounds are transformed into other olefins of different molecular weights. The disproportionation of an olefin to produce one olefin of a higher molecular weight and one olefin of a lower molecular weight can also be referred to as a self-disproportionation. For example, propene can be disproportionated to ethylene and cis- and trans-2-butene. Another type of disproportionation involves the codisproportionation of two different olefins to form still other olefins. For example, the reaction of one molecule of 2-butene with one molecule of 3-hexene can produce two molecules of 2-pentene.

Several catalyst systems have been proposed for the disproportionation of olefins. Several disadvantages have been observed for these catalyst systems. In some cases, isomerization of the double bond of the starting material or product occurs and disproportionation involving the isomeric olefin yields a mixture of products which is difficult to separate. With certain catalysts, polymerization of the olefins occurs at long reaction times or high reaction temperatures. Some catalysts cause alkylation of aromatic solvents with the olefin, thereby consuming some of the reactant or product and producing a more complex product mixture. Some catalysts are only effective for terminal olefins and other catalysts may be effective only with internal olefins. Many of the metathesis catalyst systems use expensive organoaluminum compounds or other organic complexes which present operational difficulties during production, storage, and use.

Some olefins have very close boiling points and, thus, are very difficult to separate by conventional means, such as distillation. For example, 4-methyl-1-pentene and 4-methyl-2-pentene produced by potassium on potassium carbonate catalyzed dimerization of propylene have boiling temperatures of 53.9° C. and 56.3° C., respectively. The separation of thermodynamically more stable isomer 4-methyl-2-pentene, which is lack of industrial use, from 4-methyl-1-pentene which is a monomer for poly(4-methyl-1-pentene), a high temperature polyolefin, is, therefore, very difficult by simple distillation.

There is, therefore, a need to develop a catalyst that is very effective in olefin disproportionation. There is also a need to develop a process to simplify and facilitate the separation of industrially important olefins by simple distillation from other olefins that have very close boiling points.

SUMMARY OF THE INVENTION

An object of the invention is to provide a simple disproportionation catalyst which produces very little undesirable olefin isomerization and does not require the use of expensive organoaluminum or organic complex components.

Another object of the invention is to provide a process for reacting olefins to obtain disproportionation products.

A further object of the invention is to provide a process to separate olefins having very close boiling points.

Other objects, features, and advantages of the invention will appear more fully from the following description and the claims.

According to a first embodiment of the invention, a process for the disproportionation of olefins is provided which comprises contacting an effective amount of a catalyst comprising a metal or ammonium tungsten oxide with the olefins under disproportionation conditions.

According to a second embodiment of the invention, a process is provided to separate by disproportionation at least one 1-olefin from a mixture of olefins that contain the 1-olefin and have close boiling points which comprises: (1) contacting the mixture of olefins with another 1-olefin in the presence of a disproportionation catalyst under conditions sufficient to provide a disproportionation reaction to produce disproportionation products that have significantly different boiling points among the resultant products, and (2) separating the resultant products.

DETAILED DESCRIPTION OF THE INVENTION

The process of the first embodiment of the invention involves the contacting of at least two non-conjugated olefins which may be the same or different olefins in the presence of an ammonium or metal tungsten oxide as catalyst. Typically, at least one of the olefins contains 3 to 30 carbon atoms per molecule and contains one or more double bonds.

Generally, at least one of the olefinic reactants is an acylic olefin having the formula $RCH=CHR_1$, wherein R and $R_1$ are independently selected from the group consisting of hydrogen, alkyl radicals, aryl and alkynyl radicals with each of the radicals containing 1 to 15 carbon atoms, or a monocyclic olefin represented by the formula

wherein $R_2$ is an alkylene or alkenylene radical containing 5 to 16 carbon atoms and wherein each of the radicals R, $R_1$, and $R_2$ can contain one or more halides provided the halides are at least two carbons from the carbons of olefinic bond, and each of the radicals can contain one or more aryl or alkyl-substituted aryl groups provided these groups are at least one carbon from the carbons of the olefinic bond. Preferred olefins are those wherein R and $R_1$ are selected from hydrogen and alkyl radicals containing 1 to 10 carbon atoms.

Examples of suitable olefins include propene, 1-butene, 2-butene 1-pentene, 2-pentene, 1-hexene, 2-hexene, 1-octene, 2-octene, 4-methyl-2-pentene, 4-methyl-1-pentene, 4-methyl-1-heptene, 2-decene, 6-dodecene, 1-tetradecene, 1-eicosene, 1,4-hexadiene, 4-chloro-1-butene, 4-phenyl-1-butene, 4-phenyl-1-octene, cycloheptene, cyclooctene, 4-chloro-1-cyclooctene, and other similar olefins.

When two different olefins are utilized in the disproportionation, one of the olefins, generally, must be an olefin as described above and the other olefin can be either another olefin as described above or ethylene.

When two different olefins are employed in the disproportionation process, the molar ratio of one olefin to the other olefinic reactant is not critical, and, generally, up to a 20-fold excess, preferably up to a 2-fold excess of one olefin can be employed.

The catalyst used in the first embodiment of the invention is an ammonium or metal tungsten oxide. The preferred catalyst is an ammonium or alkali metal tungen oxide. The most preferred catalyst is an ammonium or alkali metal metatungstate having the formula of $3M_2WO_4 \cdot 9WO_3H_2O$ wherein M is an ammonium ion or an alkali metal ion.

Ammonium metatungstate is commercially available from Aldrich Chemical Co. An alkali metal metatungstate can be prepared from ammonium metatungstate by treatment with an effective amount of an alkali metal hydroxide under conditions sufficient to prepare an alkali metal metatungstate. It can generally be done by titrating an ammonium metatungstate solution, from 0.001N up to saturation, with an aqueous solution of an alkali metal hydroxide, about 0.01N to 5.0N, preferably about 0.1N, until the metatungstate solution becomes slightly basic. This can be monitored by, for example, a pH meter or pH paper. The slightly basic solution can then be heat treated, for example, at about 200° C. to about 600° C., preferably about 300° C. to about 500° C. for about 1 hour to about 24 hours.

The catalyst of the first embodiment of the present invention is employed in a catalytically effective amount. The amount of catalyst employed in the process of this invention can be expressed in terms of the molar ratio of olefin to catalyst. Generally, the molar ratio of olefinic reactant to catalyst is from about 1/1 to about 5000/1 and preferably from about 50/1 to about 500/1.

The disproportionation reaction of the first embodiment of this invention can be carried out under any suitable reaction conditions in any suitable reactors. Generally, the reaction is carried out at temperatures in the range of about 200° C. to about 600° C., preferably about 300° C. to about 500° C. While lower temperatures can be used, the reaction rates are, generally, too low to be of interest.

The pressure during the disproportionation reaction is, generally, in the range of about atmospheric to about 1500 psig (10341 kiloPascals gauge-kPa). Preferably, the pressure is in the range of about atmospheric to about 500 psig (3447 kPa).

The presence of oxygen and water has been found to be deleterious to the disproportionation reaction and should be substantially avoided during the reaction. Inert gases such as nitrogen or helium can be used to maintain a dry, inert atmosphere during the reaction.

The reaction time period depends on the reaction temperature and pressure as well as on the nature of the particular catalyst system and olefin used. The reaction time is generally from about 30 minutes to several days. Preferably, the reaction time is from about 5 to about 100 hours.

The reaction product mixture from the disproportionation can be worked up using any combination of conventional separation and purification techniques. Depending on the relative volatilities of the unreacted starting olefins, the olefin products can usually be separated by, for example, fractionation distillation. The unreacted starting olefins can be recycled to the reaction zone. The olefin products in the first embodiment of the invention can be purified by conventional techniques such as crystallization, distillation, or extractions.

In the second embodiment of the invention, a process for separating a 1-olefin from a mixture of olefins that have close boiling points is provided which comprises: (1) disproportionating the olefins with another 1-olefin in the presence of a proportionation catalyst under disproportionation conditions to produce disproportionation products that have significantly different boiling points among the resultant products, and (2) separating the resultant products.

The mixture of olefins containing the 1-olefin to be separated are liquid under ambient conditions and are acyclic olefins having the formula $R_3CH=CHR_4$, wherein $R_3$ and $R_4$ are independently selected from hydrogen, alkyl radicals and alkenyl radicals with each of the radicals containing 2 to 15 carbon atoms. At least one of the olefins must be a 1-olefin, i.e., either $R_3$ or $R_4$ is a hydrogen atom. Presently, preferred olefins are those wherein $R_3$ and $R_4$ are selected from hydrogen and alkyl radicals containing 2 to 10 carbon atoms.

Examples of suitable acyclic olefins include 1-pentene, 2-pentene, 1-hexene, 4-methyl-1-pentene, 4-methyl-2-pentene, cis-2-hexene, trans-2-hexene, 1-octene, cis-2-octene, trans-2-octene, and other similar olefins.

The "another" 1-olefin employed in the disproportionation reaction for the separation of olefins is selected from the group consisting of ethylene, propene, and 1-butene. The presently preferred "another" 1-olefin is ethylene.

The molar ratio of the "another" 1-olefin to the olefins in the mixture is not critical and generally from one to one ratio and up to a 20-fold excess can be employed. Preferably, up to a 2-fold excess of the "another" 1-olefin can be employed.

The catalyst used in the process of the second embodiment can be any suitable olefin disproportionation catalyst. Examples of suitable olefin disproportionation catalysts include metal tungsten, metal molybdenum, ammonium tungsten oxide, metal tungstate, (methoxyphenylcarbene)pentacarboxyltungsten(0), molybdenum oxide, and other disproportionation catalysts.

The presently preferred catalysts are ammonium or metal tungsten oxides. The most preferred catalyst is an ammonium or alkali metal metatungstate having the formula of $3M_2WO_4 \cdot 9WO_3H_2O$, wherein M is an alkali metal or ammonium ion.

Ammonium metatungstate is commercially available from Aldrich Chemical Co. Alkali metal metatungstates can be prepared from ammonium metatungstate by treatment with alkali metal hydroxide. It can generally be done by titrating an ammonium metatungstate solution, from 0.001N up to saturation, with an aqueous solution of an alkali metal hydroxide, about 0.01N to 5.0N, preferably about 0.1N, until the metatungstate solution becomes slightly basic. This can be monitored by, for example, a pH meter or pH paper. The slightly basic solution can then be heat treated, for example, at about 200° C. to about 600° C., preferably about 300° C. to about 500° C. for about 1 hour to about 24 hours.

The catalyst of the second embodiment of the present invention is employed in a catalytically effective amount. The amount of catalyst employed in the process of this invention can be expressed in terms of the molar ratio of olefin to catalyst. Generally, the molar ratio of olefinic reactant to catalyst is from about 1/1 to about 5000/1 and preferably from about 50/1 to about 500/1.

The disproportionation reaction of the second embodiment of this invention can be carried out under any suitable reaction conditions. Generally, the reaction is carried out at temperatures in the range of about 200° C. to about 600° C., preferably about 300° C. to about 500° C. While lower temperatures can be used, the reaction rates are, generally, too low to be of interest.

The pressure during the disproportionation reaction is, generally, in the range of about atmospheric to about 1500 psig (10341 kiloPascals gauge-kPa). Preferably, the pressure is in the range of about atmospheric to about 500 psig (3447 kPa).

The presence of oxygen and water has been found to be deleterious to the disproportionation reaction and should be substantially avoided during the reaction. Inert gases such as nitrogen or helium can be used to maintain a dry, inert atmosphere during the reaction.

The reaction time period depends on the reaction temperature and pressure as well as on the nature of the particular catalyst system and olefin used. The reaction time is, generally, from about 30 minutes to several days. Preferably, the reaction time is from about 5 to about 100 hours.

The reaction product mixture from the disproportionation can be worked up using any combination of conventional separation and purification techniques. Depending on the relative volatilities of the unreacted starting olefins, the olefin products can usually be separated by, for example, fractionation distillation. The unreacted starting olefins can be recycled to the reaction zone. The olefin products can be purified by conventional techniques such as crystallization, distillation, or extractions.

According to the process, two olefinic reactants are disproportionated to form a product containing 2 olefins having a total number of carbon atoms equal to the total number of carbon atoms of the two olefinic reactants and having a number of ethylenic double bonds equal to the sum of the ethylenic double bonds of the reactants. This is shown in the following reaction (I):

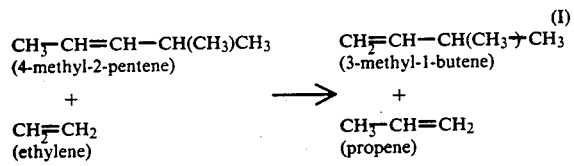

However, when a 1-olefin, such as 4-methyl-1-pentene, and ethylene, another 1-olefin, are disproportionated, the eaction product still contains the same olefins as shown in the following re ction (II):

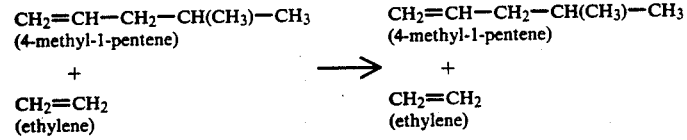

It is clear that the desired 1-olefin (4-methyl-1-pentene) in reaction (II) remains the same after disproportionation reaction with ethylene. However, the undesirable 4-methyl-2-pentene in reaction (I) is converted to 3-methyl-1-butene which has a much lower boiling point than that of 4-methyl-1-pentene and has utility as precursors of polymer or copolymers. The desired 1-olefin, here, 4-methyl-1-pentene, can, therefore, be easily separated from the product mixture by conventional means, such as distillation. Additionally, another useful 1-olefin, such as 3-methyl-1-butene is also produced by means of the second embodiment of the invention.

EXAMPLES

These examples are provided to further assist a person skilled in the art with understanding this invention. The particular reactants, conditions, and the like, are intended to be generally illustrative of this invention and are not meant to be construed as unduly limiting the reasonable scope of this invention.

EXAMPLE I

This example illustrates the procedure for preparing an alkali metal metatungstate from ammonium metatungstate.

Ammonium metatungstate (1.60 g; obtained from Aldrich) was dissolved in deionized water to make 22.0 milliliters of solution. The ammonium metatungstate solution was subsequently titrated with an alkali metal hydroxide solution described in Example II (1.0N; ca 2.0 mL) until the solution became slightly basic (ca, PH=7-8). To the resulting aqueous solution, it was added aluminum oxide (G-57; 20.0 g; 20–40 mesh) while stirring for 30 minutes. The water of the resultant reaction slurry was stripped off with an aspirator to form a damp cake which was then transferred to a porcelain dish and calcined in an oven at 350° C. for 3 hours to give the corresponding alkali metal metatungstate. The calcined material (1.50 g) was well mixed with aluminum oxide (R-268; 5.0 g; 14–20 mesh) and subsequently packed into the reactor.

EXAMPLE II

This example illustrates the use of alkali metal and ammonium metatungstates as catalysts for the disproportionation and the results of using these catalysts.

A fixed bed reactor charged with an alkali metal or ammonium metatungstate (1.5 g) catalyst mixed with aluminum oxide (5.0 g), as described in Example 1, was heated to 450° C. in the presence of an air flow for 5 hours and then purged with carbon monoxide several times. The carbon monoxide pressure was held at 125 psig for 30 minutes and the reactor was subsequently cooled down to ambient temperature in the presence of a nitrogen flow. Ethylene (150 liters per hour) and 4-methyl-2-pentene (2.0 milliliters of liquid per minute) were continuously added from the top of the reactor. The reaction temperature was controlled at 350°–400° C. by an electric heating jacket. The reaction pressure was controlled at 300 psig using a back pressure regulator. The reaction sample was taken from the bottom of the reactor (before the back pressure regulator) by withdrawing the gas-liquid mixture using a gas tight syringe.

The results of disproportionation were determined on samples taken after a two-hour reaction time, using an HP 5890 II gas chromatograph equipped with a 60 meter DB-1 capillary column. The temperature profile was set at 30° C. initially with a 15° per minute increase in the temperature until a temperature of 285° C. was reached. This final temperature was then held for 13 minutes. Detection was accomplished with a flame ionization detector in the area percent mode. Selectivity of 1-olefins and the weight percent distributions were determined by this method. Catalyst productivity is defined as the oligomerized products (i.e. $C_4$ and higher) produced per gram of nickel per hour. This was determined by the totalizer readings on the ethylene flow meter. All olefins were identified by comparison with commercially obtained samples. The results are shown in Table I below.

TABLE I

| | | Disproportionation of 4-methyl-2-pentene | | | | | |
|---|---|---|---|---|---|---|---|
| Run | Tungstate Catalyst | Reaction Temp. (°C.) | Conversion (%) | Product (Weight %)$^a$ | | | | Selectivity |
| | | | | 2MP2$^b$ | 3MB1$^c$ | 2MB1$^d$ | 2MB2$^e$ | (3MB1/MB$^f$, %) |
| 1 | NH4 | 350 | 68 | 19 | 26 | 6 | 17 | 53 |
| 2 | NH4 | 350 | 72 | 16 | 30 | 7 | 19 | 54 |
| 3 | K | 400 | 83 | 3 | 53 | 8 | 19 | 66 |
| 4 | K | 400 | 81 | 4 | 53 | 7 | 17 | 69 |
| 5 | K | 400 | 78 | 5 | 50 | 7 | 16 | 69 |
| 6 | Li | 400 | 76 | 11 | 38 | 8 | 19 | 59 |
| 7 | Li | 400 | 78 | 11 | 37 | 9 | 21 | 55 |
| 8 | Na | 400 | 87 | 5 | 66 | 5 | 11 | 81 |
| 9 | Na | 400 | 89 | 4 | 69 | 5 | 11 | 81 |

$^a$Propylene, derived from ethylene, is not included in the calculation of product weight %.
$^b$2MP2, 2-methyl-2-pentene, isomerized product of 4-methyl-2-pentene.
$^c$3MB1, 3-methyl-1-butene.
$^d$2MB1, 2-methyl-1-butene.
$^e$2MB2, 2-methyl-2-butene.
$^f$MB, methyl butenes, including 3MB1, 3MB2, and 2MB2.

Table II indicates that ammonium and alkali metal salts of metatungstate are, generally, good disproportionation catalysts with a high conversion rate and high selectivity to the 3MB1, a useful olefin. Of the tests conducted, sodium metatungstate (Runs 8–9) exhibited the highest conversion (87–89%) and selectivity to 3MB1 (81%).

EXAMPLE III

This example demonstrates that a 1-olefin can be made easier to separate from a mixture of olefins by disproportionation.

The disproportionation was carried out with 1.5 g of sodium metatungstate (mixed with 5.0 grams of aluminum oxide) by the procedure identical to that disclosed in Example II with the exception that a mixture of 4-methyl-1-pentene(4MP1) and 4-methyl-2-pentene(4MP2) instead of pure 4-methyl-2-pentene was used as feed. The reaction products were then separated by distillation. The results are shown in Table II below.

TABLE II

| | Disproportionation of 4MP1 and 4MP2 | | | | |
|---|---|---|---|---|---|
| | Feed (Wt. %)$^a$ | | Metatungstate | Reaction Temp. | Distillation Products (Weight %) |
| Run | 4MP1 | 4MP2 | Catalyst | (°C.) | 4MP1 | 4MP2 |
| 10 | 91 | 9 | Li | 400 | 99 (95) | 1 (5) |
| 11 | 90 | 10 | Na | 375 | 99 (95) | 1 (5) |
| 12 | 91 | 9 | Na | 400 | 99 (95) | 1 (5) |
| 13 | 92 | 8 | Na | 425 | 99 (96) | 1 (4) |
| 14 | 93 | 7 | K | 375 | 99 (96) | 1 (4) |
| 15 | 91 | 9 | K | 400 | 99 (96) | 1 (4) |

$^a$Feed composition was determined by GC analyses as described in Example II.
$^b$The composition of products was determined by distillation followed by GC analyses as described in Example II. The mixture of products (100 ml) was distilled at 54–56° C. under ambient pressure using a 2-ft. distillation column with a 1/5 distillation rate. The values in the parentheses are data for control runs representing the composition of the portion of feed that was distilled using the same procedure without disproportionation process. Propylene, derived from ethylene, is not included in the calculation of product weight %.

The results shown in Table II clearly demonstrate that the ratio of 4MP1 to 4MP2 improved from as high as 90 to 10 (Run 11) to 99 to 1 after disproportionation process. Hoever, the ratio of 4MP1 to 4MP2 remained high (95 to 5) for the control run that was not disproportionated. A high ratio of 4MP1 to 4MP2 facilitates the separation of these two olefinic isomers.

The results shown in the above examples further demonstrate that the present invention is well adapted to carry out the objects and attain the ends and advantages mentioned as well as those inherent therein.

These examples merely illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A process for disproportionation of olefins, under disproportionation conditions, comprising contacting a catalyst consisting of a metal tungsten oxide or ammonium tungsten oxide with said olefins to catalyze said disproportionation.

2. A process according to claim 1 wherein said metal tungsten oxide is an alkali metal tungsten oxide.

3. A process according to claim 2 wherein said alkali metal tungsten oxide is an alkali metal metatungstate.

4. A process according to claim 3 wherein said alkali metal metatungstate is prepared by contacting said ammonium metatungstate with an effective amount of an alkali metal hydroxide under conditions sufficient to prepare an alkali metal metatungstate.

5. A process according to claim 4 wherein said alkali metal metatungstate is sodium metatungstate.

6. A process according to claim 1 wherein said ammonium tungsten oxide is ammonium metatungstate.

7. A process for disproportionation of olefins comprising contacting a catalyst consisting of a metal or ammonium tungsten oxide with said olefins under disproportionation conditions wherein said catalyst is present in an amount such that a molar ratio of said olefins to said catalyst is from about 1/1 to about 5000/1.

8. A process according to claim 7 wherein said ratio is from about 50/1 to about 500/1.

9. A process according to claim 1 wherein said conditions are in the range of about 200° C. to about 600° C. and of about atmospheric pressure to about 1500 psig.

10. A process according to claim 9 wherein said conditions are in the range of about 300° C. to about 500° C. and of about atmospheric pressure to about 500 psig.

11. A process according to claim 8 wherein said conditions are in the range of about 300° C. to about 500° C. and of about atmospheric pressure to about 500 psig.

12. A process for separating at least one 1-olefin from a mixture with other olefins, said process comprising: (1) contacting said mixture with another 1-olefin in the presence of a disproportionation catalyst under disproportionation conditions to convert said olefins and said another 1-olefin to disproportionation products and (2) separating said at least one 1-olefin from said disproportionation products by distillation.

13. A process according to claim 12 wherein said disproportionation catalyst comprises a metal or ammonium tungsten oxide.

14. A process according to claim 13 wherein said metal tungsten oxide is an alkali metal tungsten oxide.

15. A process according to claim 14 wherein said alkali metal tungsten oxide is an alkali metal metatungstate.

16. A process according to claim 15 wherein said alkali metal metatungstate is sodium metatungstate.

17. A process according to claim 13 wherein said ammonium tungsten oxide is ammonium metatungstate.

18. A process according to claim 12 wherein said mixture of olefins comprises at least an 1-olefin selected from the group consisting of 4-methyl-1-pentene, 1-butene, 1-hexene, and 1-octene.

19. A process according to claim 18 wherein said 1-olefin is 4-methyl-1-pentene.

20. A process according to claim 12 wherein said another 1-olefin is selected from the group consisting of ethylene, propene and 1-butene.

21. A process according to claim 20 wherein said another 1-olefin is ethylene.

22. A process according to claim 12 wherein said amount of catalyst is expressed in terms of molar ratio of olefin to said catalyst and said ratio is from about 1/1 to about 5000/1.

23. A process according to claim 22 wherein said ratio is from about 50/1 to about 500/1.

24. A process according to claim 12 wherein said conditions are in the range of about 200° C. to about 600° C. and of about atmospheric pressure to about 1500 psig.

25. A process according to claim 24 wherein said conditions are in the range of about 300° C. to about 500° C. and of about atmospheric pressure to about 500 psig.

26. A process according to claim 23 wherein said conditions are in the range of about 300° C. to about 500° C. and of about atmospheric pressure to about 500 psig.

27. A process for separating 4-methyl-1-pentene from a mixture of 4-methyl-1-pentene and 4-methyl-2-pentene comprising:
(a) adding ethylene to said mixture;
(b) contacting said mixture with a disproportionation catalyst;
(c) controlling said mixture at 350°-400° C. and 300 psig to produce disproportionation products comprising 4-methyl-1-pentene, 3-methyl-1-butene, propylene, and ethylene; and
(d) separating said 4-methyl-1-pentene from said 3-methyl-1-butene, said propylene and said ethylene.

* * * * *

UNITED STATES PATENT AND TRADEMARK OFFICE
CERTIFICATE OF CORRECTION

PATENT NO. : 5,162,597
DATED : November 10, 1992
INVENTOR(S) : An-hsiang Wu

It is certified that error appears in the above-identified patent and that said Letters Patent is hereby corrected as shown below:

Column 2, line 20, after "1-olefin", please insert ---which is not present in said mixture---.

Column 9, line 21, please delete "with" and insert ---comprising---.

Column 9, line 22, after "1-olefin", please insert ---which is not present in said mixture---.

Column 9, line 24, after "said", please insert ---other---.

Column 9, lines 24 & 25, please delete "and said another 1-olefin".

Column 9, line 41, please delete "mixture of olefins comprises".

Column 9, line 41, please delete "an", and insert ---one---.

Column 9, line 41, after "1-olefin", please insert ---is---.

Column 10, line 4, after "said", please insert ---at least one---.

Signed and Sealed this

Nineteenth Day of October, 1993

Attest:

BRUCE LEHMAN

Attesting Officer        Commissioner of Patents and Trademarks

UNITED STATES PATENT AND TRADEMARK OFFICE
CERTIFICATE OF CORRECTION

PATENT NO. : 5,162,597
DATED      : Nov. 10, 1992
INVENTOR(S) : An-hsiang Wu

It is certified that error appears in the above-identified patent and that said Letters Patent is hereby corrected as shown below:

Column 2, line 45, formula should read:

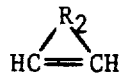

Signed and Sealed this

Second Day of November, 1993

Attest:

BRUCE LEHMAN

Attesting Officer

Commissioner of Patents and Trademarks